(12) United States Patent
Kodama et al.

(10) Patent No.: US 12,140,470 B2
(45) Date of Patent: Nov. 12, 2024

(54) BIOMETRIC INFORMATION MEASURING DEVICE

(71) Applicant: TANITA CORPORATION, Itabashi-ku (JP)

(72) Inventors: Miyuki Kodama, Itabashi-ku (JP);
Miyuki Izumi, Itabashi-ku (JP);
Hirokazu Ono, Itabashi-ku (JP)

(73) Assignee: TANITA CORPORATION, Itabashi-ku (JP)

( * ) Notice: Subject to any disclaimer, the term of this patent is extended or adjusted under 35 U.S.C. 154(b) by 503 days.

(21) Appl. No.: 17/436,898

(22) PCT Filed: Mar. 3, 2020

(86) PCT No.: PCT/JP2020/008907
§ 371 (c)(1),
(2) Date: Sep. 7, 2021

(87) PCT Pub. No.: WO2020/184293
PCT Pub. Date: Sep. 17, 2020

(65) Prior Publication Data
US 2022/0136890 A1 May 5, 2022

(30) Foreign Application Priority Data

Mar. 12, 2019 (JP) .................... 2019-044559

(51) Int. Cl.
*G01G 19/44* (2006.01)
*G01G 19/34* (2006.01)

(52) U.S. Cl.
CPC ............ *G01G 19/44* (2013.01); *G01G 19/34* (2013.01)

(58) Field of Classification Search
CPC ........ G01G 19/44; G01G 19/34; G01H 40/63; A61B 5/4872; A61B 5/7275;
(Continued)

(56) References Cited

U.S. PATENT DOCUMENTS 6,038,315 A * 3/2000 Strait ................. H04L 9/304
713/186
6,526,315 B1 * 2/2003 Inagawa ............ A61B 5/0537
600/547

(Continued)

FOREIGN PATENT DOCUMENTS

| JP | 2006-102308 A | 4/2006 |
| JP | 2007-296093 A | 11/2007 |
| JP | 2015-51224 A | 3/2015 |

OTHER PUBLICATIONS

International Search Report issued on Jun. 2, 2020 in PCT/JP2020/008907 filed on Mar. 3, 2020, 2 pages.

*Primary Examiner* — Jacques M Saint Surin
(74) *Attorney, Agent, or Firm* — Oblon, McClelland, Maier & Neustadt, L.L.P.

(57) ABSTRACT

A biometric information measuring device comprising a control part that determines a degree of matching with respect to a purpose of use that is set in measured data related to multiple body compositions, based on a purpose-of-use matching degree relationship in which a degree of matching with respect to a purpose of use is associated according to a combination relationship about change directions of data related to the multiple body compositions associated by a display order with respect to the purpose of use.

20 Claims, 15 Drawing Sheets

(58) Field of Classification Search
CPC .......... A61B 5/1036; A61B 2562/0209; G16H 20/30; G16H 20/60; G16H 50/30; G16H 40/63
USPC ...................................................... 177/25.12
See application file for complete search history.

(56) References Cited

U.S. PATENT DOCUMENTS

| | | | | |
|---|---|---|---|---|
| 6,782,340 | B1 * | 8/2004 | Komatsu | A61B 5/4872 |
| | | | | 177/246 |
| 7,602,301 | B1 * | 10/2009 | Stirling | A61B 5/22 |
| | | | | 340/573.7 |
| 7,821,407 | B2 * | 10/2010 | Shears | A61B 5/6804 |
| | | | | 73/379.01 |
| 7,844,081 | B2 * | 11/2010 | McMakin | G01S 13/887 |
| | | | | 382/115 |
| 7,978,081 | B2 * | 7/2011 | Shears | A61B 5/11 |
| | | | | 73/379.01 |
| 8,475,367 | B1 * | 7/2013 | Yuen | G16H 50/30 |
| | | | | 177/4 |
| 9,237,863 | B2 * | 1/2016 | Shimizu | A61B 5/4872 |
| 11,219,396 | B2 * | 1/2022 | Berg | A61B 5/6804 |
| 2009/0089672 | A1 | 4/2009 | Tseng et al. | |

* cited by examiner

Purpose of use "Diet" (male)

| First item ⊿body fat percentage | Second item ⊿body age | Third item ⊿basal metabolic rate | purpose matching degree evaluation rank order | purpose matching degree evaluation data |
|---|---|---|---|---|
| − Change | − | + | 1 | 100 points |
| | | ± | 2 | |
| | | − | 3 | |
| | ± | + | 4 | |
| | | ± | 5 | |
| | | − | 6 | |
| | + | + | 7 | |
| | | ± | 8 | |
| | | − | 9 | |
| ± Substantially no change | − | + | 10 | |
| | | ± | 11 | |
| | | − | 12 | |
| | ± | + | 13 | |
| | | ± | 14 | |
| | | − | 15 | |
| | + | + | 16 | |
| | | ± | 17 | |
| | | − | 18 | |
| + Change | − | + | 19 | |
| | | ± | 20 | |
| | | − | 21 | |
| | ± | + | 22 | |
| | | ± | 23 | |
| | | − | 24 | |
| | + | + | 25 | |
| | | ± | 26 | |
| | | − | 27 | Less than 50 points |

Fig.5

Fig.6A
<Purpose of use is "Diet" and there are favorable changes: high rank order>
Very smooth changes in body compositions that suit your purpose! You have a good lifestyle. It's a little more to reach your goal. Continue to do your best at this pace! But don't overdo it.

Fig.6B
< Purpose of use is "Diet" and fat is reduced but basal metabolism is decreased: medium rank order>
You are losing body fat, but it is worrisome that your basal metabolism is declining. Have you extremely over reduced diet? A well-balanced diet and exercise are important for increasing metabolism! Please review your lifestyle to see if you are taking protein properly and if you are inactive.

<1> 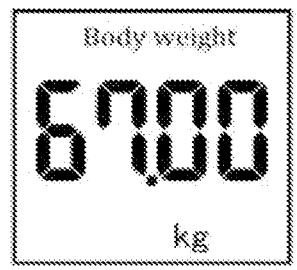
<5> 
<2> 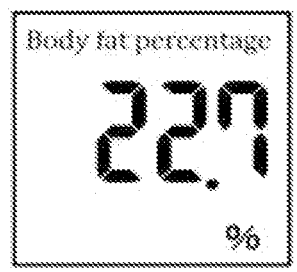
<6> 
<3> 
<7> 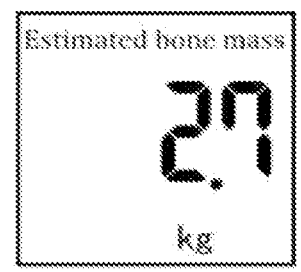
<4> 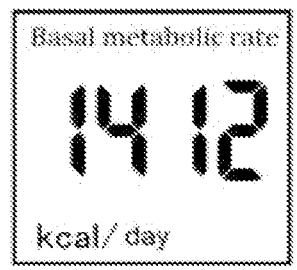
<8> 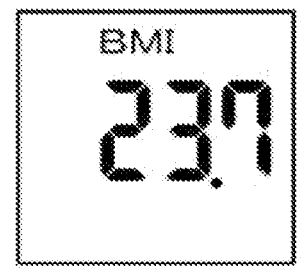
Fig.9

AD1 17

< Advice>
This is a display order in which, in order to be healthy and slim, the items that you are concerned about their changes or the items that you want to pay attention to are ranked high. Obesity does not mean that you are overweight, but that you have a high body fat percentage. Even if you have lost weight, you haven't lost body fat, and if you lose muscles or bones, which are important tissues for your body, it will cause rebound. If you lose body fat in a healthy way, your body age will become younger and your basal metabolism rate will also be increased, so let's be encouraged and aim for a body that is hard to gain weight.

<Body composition change comprehensive evaluation>
Since there is no previous measurement result data, it cannot be determined this time. It will be determined from the next time.

<1>
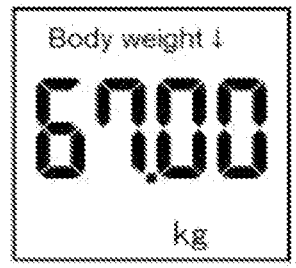
<2>
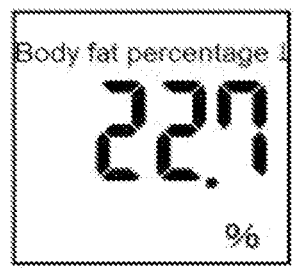
<3>
<4>
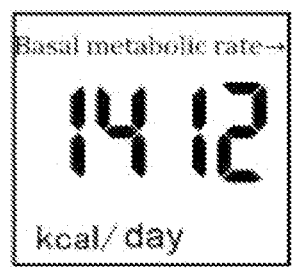
<5>
<6>
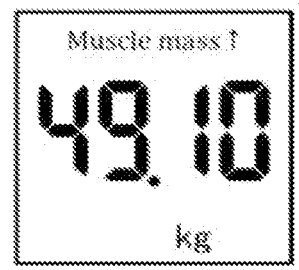
<7>
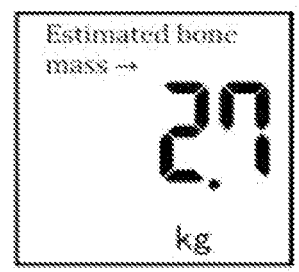
<8>
Fig.11

AD5

< Advice>
Very smooth changes in body compositions that suit your purpose!

You have a good lifestyle. It's a little more to reach your goal.

Continue to do your best at this pace! But don't overdo it.

| Body composition change comprehensive evaluation | | ■■■■■■■ | 90 points |
|---|---|---|---|
| Body composition change: Element evaluation | | | |
| First element | body fat percentage ↓ | * * * * * * * * * * | 99 points |
| Second element | body age ↓ | * * * * * * * | 95 points |
| Third element | basal metabolic → | * * * * * | 80 points |

Fig.12

Purpose of use "I want to exercise and have a firm body"

| First item Δmuscle mass | Second item Δbody fat percentage | Third item Δbasal metabolic rate | purpose matching degree evaluation rank order | purpose matching degree evaluation data |
|---|---|---|---|---|
| + Change | − | + | 1 | 100 points |
| | | ± | 2 | |
| | | − | 3 | |
| | ± | + | 4 | |
| | | ± | 5 | |
| | | − | 6 | |
| | + | + | 7 | |
| | | ± | 8 | |
| | | − | 9 | |
| ± Substantially no change | − | + | 10 | |
| | | ± | 11 | |
| | | − | 12 | |
| | ± | + | 13 | |
| | | ± | 14 | |
| | | − | 15 | |
| | + | + | 16 | |
| | | ± | 17 | |
| | | − | 18 | |
| − Change | − | + | 19 | |
| | | ± | 20 | |
| | | − | 21 | |
| | ± | + | 22 | |
| | | ± | 23 | |
| | | − | 24 | |
| | + | + | 25 | |
| | | ± | 26 | |
| | | − | 27 | Less than 50 points |

Fig. 13

<Purpose of use is "I want to exercise and have a firm body" and there is no significant change: medium rank order>

Overall there is no significant change and it is in a maintenance trend. The point is to gain more muscle to get closer to your goal! Increase the amount of exercise and consume protein within 45 minutes after exercising whenever possible!

Fig.14

Purpose of use "Health maintenance"

| First item | Second item | Third item | purpose matching degree evaluation rank order |
|---|---|---|---|
| Δbody fat percentage | Δvisceral fat level | Δbody age | |
| − Change | − | + | 1 |
| | | ± | 2 |
| | | − | 3 |
| | ± | + | 4 |
| | | ± | 5 |
| | | − | 6 |
| | + | + | 7 |
| | | ± | 8 |
| | | − | 9 |
| ± Substantially no change | − | + | 10 |
| | | ± | 11 |
| | | − | 12 |
| | ± | + | 13 |
| | | ± | 14 |
| | | − | 15 |
| | + | + | 16 |
| | | ± | 17 |
| | | − | 18 |
| + Change | − | + | 19 |
| | | ± | 20 |
| | | − | 21 |
| | ± | + | 22 |
| | | ± | 23 |
| | | − | 24 |
| | + | + | 25 |
| | | ± | 26 |
| | | − | 27 | purpose matching degree evaluation data 100 points ↓ Less than 50 points

Fig.15

Purpose of use "Diet" (female)

| First item<br>⊿body fat mass | Second item<br>⊿body age | Third item<br>⊿basal metabolic rate | purpose matching degree evaluation rank order |
|---|---|---|---|
| − Change | − | + | 1 |
| | | ± | 2 |
| | | − | 3 |
| | ± | + | 4 |
| | | ± | 5 |
| | | − | 6 |
| | + | + | 7 |
| | | ± | 8 |
| | | − | 9 |
| ± Substantially no change | − | + | 10 |
| | | ± | 11 |
| | | − | 12 |
| | ± | + | 13 |
| | | ± | 14 |
| | | − | 15 |
| | + | + | 16 |
| | | ± | 17 |
| | | − | 18 |
| + Change | − | + | 19 |
| | | ± | 20 |
| | | − | 21 |
| | ± | + | 22 |
| | | ± | 23 |
| | | − | 24 |
| | + | + | 25 |
| | | ± | 26 |
| | | − | 27 | purpose matching degree evaluation data 100 points ↓ Less than 50 points

Fig.16

BIOMETRIC INFORMATION MEASURING DEVICE

CROSS-REFERENCE TO RELATED APPLICATIONS

The present application is a 35 U.S.C. § 371 national stage patent application of International patent application PCT/JP2020/008907, filed on Mar. 3, 2020, which is based on and claims the benefits of priority to Japanese Application No. 2019-044559, filed on Mar. 12, 2019. The entire contents of these applications are incorporated herein by reference.

TECHNICAL FIELD

The present invention relates to a biometric information measuring device.

TECHNICAL BACKGROUND

A weight scale has been improved, and a biometric information measuring device referred to as a body composition analyzer that also measures biometric information other than a body weight has become popular. For example, Patent Document 1 listed below describes a biometric information measuring device that displays measurement results in an order corresponding to a purpose of use of the biometric information measuring device.

RELATED ART

Patent Document

Patent Document 1: Japanese Patent Application Laid-Open Publication No. 2007-296093.

SUMMARY OF THE INVENTION

Problems to Be Solved by the Invention

The biometric information measuring device described in Patent Document 1 only displays measurement results in an order corresponding to a purpose of use of the biometric information measuring device, and a user of the biometric information measuring device has no choice but to self-determine whether a change in his/her body(more specifically, a body composition, which is a physical indicator) is favorable or not with respect to a purpose of use. In particular, when a user has no professional knowledge, since the user cannot understand where to pay attention to in the measurement results of the body compositions, the user only loosely knows the measurement results, and it is difficult for the user to determine whether or not a change in his/her body is favorable with respect to a purpose of use.

Therefore, one purpose of the present invention is to provide a biometric information measuring device that allows a user to determine whether or not a change in a body composition of the user obtained by the biometric information measuring device is favorable with respect to a purpose of use of the body composition analyzer.

Means for Solving the Problems

In order to solve the above problem, the present invention provides a biometric information measuring device including a control part that determines a degree of matching with respect to a purpose of use that is set in measured data related to multiple body compositions, based on a purpose-of-use matching degree relationship in which a degree of matching with respect to a purpose of use is associated according to a combination relationship about change directions of data related to the multiple body compositions associated by a display order with respect to the purpose of use.

Effect of Invention

According to at least an embodiment of the present invention, how well a change in body composition data matches a purpose of use of the body composition analyzer can be determined.

BRIEF DESCRIPTION OF DRAWINGS

FIG. 5 illustrates an example of a purpose-of-use matching degree relationship according to the embodiment.
FIGS. 6A and 6B are for describing specific examples of advice information associated with a purpose matching degree evaluation rank order.
FIG. 9 illustrates an example of a display mode of measurement result data of body compositions when there is no previous measurement result data of the body compositions.
FIG. 10 illustrates an example of advice information and the like when there is no previous measurement result data of the body compositions.
FIG. 11 illustrates an example of a display mode of measurement result data of body compositions when there is previous measurement result data of the body compositions.
FIG. 12 is for describing a display example of body composition change comprehensive evaluation and advice information.
FIG. 13 is for describing a modified embodiment.
FIG. 14 is for describing a modified embodiment.
FIG. 15 is for describing a modified embodiment.
FIG. 16 is for describing a modified embodiment.

In the following, an embodiment and the like of the present invention are described with reference to the drawings. The description will be given in the following order:

EMBODIMENT

Modified Embodiments

The embodiment and the like described below are preferred examples of the present invention, and the content of the present invention is not limited to the embodiment and the like.

Embodiment

In the following, an embodiment of the present invention is described in detail with reference to the drawings. In the embodiment described below, an example is described in which the present invention is applied to a biometric information measuring device (hereinafter, referred to as a body composition analyzer as appropriate) that measures data about body compositions (hereinafter, referred to as body composition data as appropriate). Examples of types of body compositions include body weight, fat percentage, visceral fat level, body water content, muscle mass, basal metabolic rate, bone mass, lean body mass, somatic cell mass, visceral fat area, BMI, obesity level, intracellular fluid volume, extracellular fluid volume, and the like. The present embodiment is described using, as the types of body compositions, "body weight," "body fat percentage or body fat mass," "body age" (an indicator that is obtained based on basal metabolism, body fat and body weight and shows an age of a body composition it is close to), "basal metabolic rate," "visceral fat level," "muscle mass," "estimated bone mass" and "BMI." The body composition data is acquired by the body composition analyzer by performing commonly known measurements and computations.

[Body Composition Analyzer]
(External Shape of Body Composition Analyzer)

Figure 1:
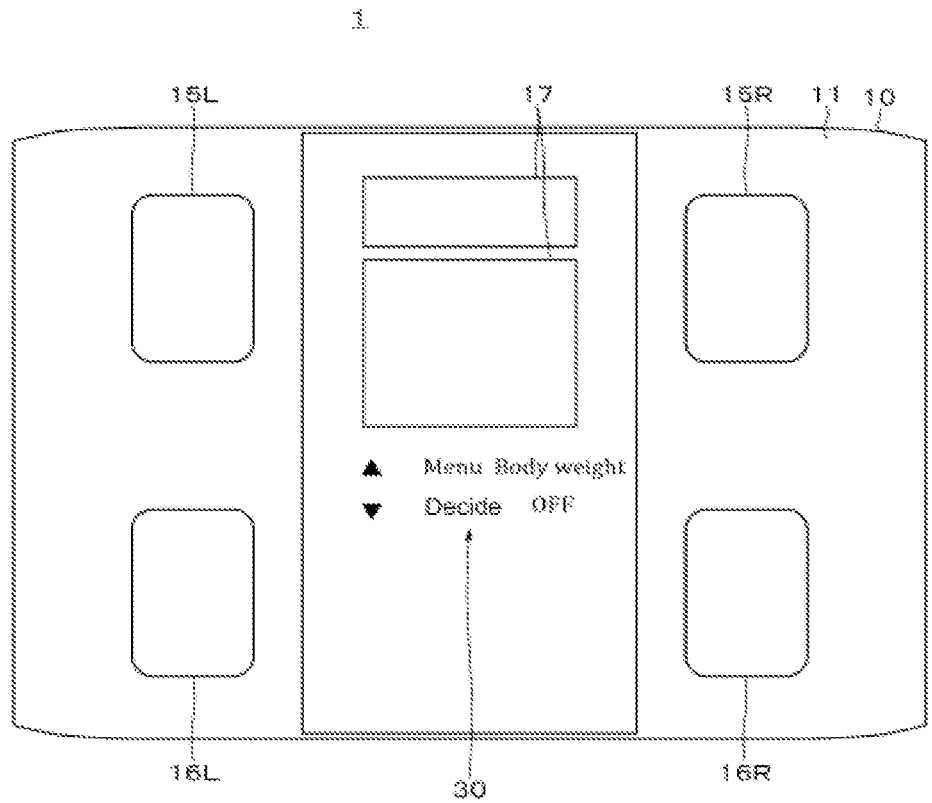
FIG. 1 illustrates an external shape of a body composition analyzer according to an embodiment.

FIG. 1 illustrates an external shape of a body composition analyzer according to the embodiment of the present invention. As illustrated in FIG. 1, in a body composition analyzer 1, electrodes, a display part and an operation part are formed on an upper surface 11 of a stand 10, which is for a user to get on.

The upper surface 11 of the stand 10 is formed substantially flat for the user to get on. The upper surface 11 of the stand 10 is a standing area with which the soles of the feet, which are parts of user's body, are in contact when body composition data is measured, and, on the upper surface 11, a current supply electrode (15R), a current supply electrode (15L), a voltage measurement electrode (16R) and a voltage measurement electrode (16L), which are each formed of a metal plate, are formed apart from each other. The electrodes do not have to be each a metal plate as long as the electrodes are conductive. The electrodes are not particularly limited. However, when the electrodes are each formed of a metal plate as described above, a user can easily recognize positions where to place the user's feet.

The current supply electrode (15R) and the current supply electrode (15L) are electrodes for supplying a current from parts of a user's body (for example, the toe sides of the soles of the feet) that are in contact with the electrodes into the user's body. On the other hand, the voltage measurement electrode (16R) and the voltage measurement electrode (16L) are electrodes for detecting a voltage generated between parts of the user's body (for example, between the heel side of the sole of the right foot and the heel side of the sole of the left foot) that are in contact with the electrodes. Based on values of the supplied current and the detected voltage, a bioimpedance of the user can be determined. In the embodiment, the toe side of the sole of the right foot of the user is in contact with the current supply electrode (15R), and the heel side of the sole of the right foot of the user is in contact with the voltage measurement electrode (16R). Further, the toe side of the sole of the left foot of the user is in contact with the current supply electrode (15L), and the heel side of the sole of the left foot of the user is in contact with the voltage measurement electrode (16L).

A display part 17 is provided on the upper surface of the stand 10. As the display part 17, an LCD (Liquid Crystal Display), an organic EL (Electro Luminescence) display, or the like can be applied. As illustrated in FIG. 1, the display part 17 according to the present embodiment has two displays. Display contents described below are displayed, for example, in a lower side display of the display part 17. The display part 17 may have one or three or more displays, and may be a display separate from the body composition analyzer 1. When the display part 17 is a display separate from the body composition analyzer 1, the measurement results of the body compositions are transmitted from the body composition analyzer 1 to the display part 17 by wired or wireless communication. Then, the measurement results of the body compositions are received and displayed by the display part 17. The display part 17 may be a display of a smartphone or a personal computer held by the user.

An operation part 30 that receives various inputs is provided on the upper surface of the stand 10. For example, the operation part 30 is provided below the display part 17 near a center of the body composition analyzer 1. As a result, it can prevent the user from accidentally operating the operation part 30 with the soles of his/her feet and inputting an unintended operation when the user places his/her feet on the stand 10. Further, by forming the operation part 30 and the display part 17 along an approach direction of the user, the user can perform an input operation with respect to the operation part 30 and perform setting of the user's date of birth and the like while confirming the display of the display part 17.

In the above, an example of the external appearance of the body composition analyzer 1 has been described. The user raises one foot and puts the foot on one pair of electrodes (for example, the current supply electrode (15R) and the voltage measurement electrode (16R)) formed on the upper surface 11. Next, the user raises the other foot and puts the foot on the other pair of electrodes (for example, the current supply electrode (15L) and the voltage measurement electrode (16L)) formed on the top surface 11. Then, measurement of the user's body composition data is started.

[Operation Part]

Figure 2:
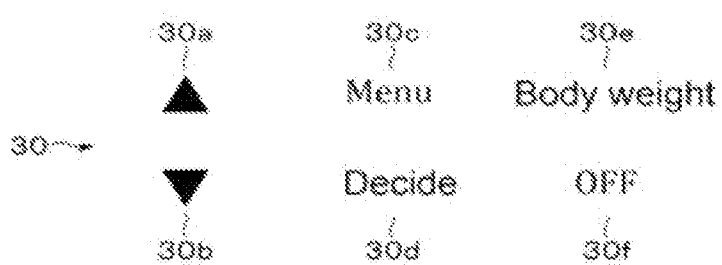
FIG. 2 is for describing a structure of an operation part according to the embodiment.

The operation part 30 according to the present embodiment includes six touch switches (a touch switch (30a), a touch switch (30b), a touch switch (30c), a touch switch (30d), a touch switch (30e) and a touch switch (30f)), and these touch switches are arranged in the manner illustrated in FIG. 2. The number and arrangement positions of the touch switches of the operation part 30 can be changed as appropriate. The operation part 30 is not limited to the touch switches, but may be mechanical switches (for example, push switches to be pressed by the user).

Here, an example of functions assigned to the touch switches forming the operation part 30 is described. The touch switch (30a) and the touch switch (30b) are respectively an up key and a down key for increasing or decreasing a numerical value. The touch switch (30c) is a menu key that displays a menu. The touch switch (30d) is a decision key that is used when a selection is decided. After the touch switch (30c) is touched, by touching the touch switch (30a) or the touch switch (30b), menu items such as (1) call measurement, (2) guest measurement, (3) previous value, (4) speed change of result display, (5) setting of purpose of use, (6) display selection of measurement results, (7) data registration, (8) data deletion, (9) change of date and time, and (10) regional change are switched. Then, by touching the touch switch (30d), the user can set one of the menu items. In this case, when the number of registered users of data is 0, the above-described menu item (1), menu item (3), menu item (4), menu item (5), menu item (6) and menu item (8) are not displayed. Further, when the registered data is 17 years old or younger, the menu item (5) is not displayed.

The touch switch (30*e*) is a body weight key that is used when the user only wants to measure his/her weight. After the touch switch (30*e*) is touched, when the user gets on the body composition analyzer 1, only the user's body weight is measured. The touch switch (30*f*) is an OFF key that is used when power supply is turned off or when setting or measurement is interrupted. For example, in a stage of selecting a menu item described above, when the user wants to interrupt the selection, the user can press the touch switch (30*f*).

"Example of Internal Structure (Electrical Structure) of the Body Composition Analyzer"

Figure 3:
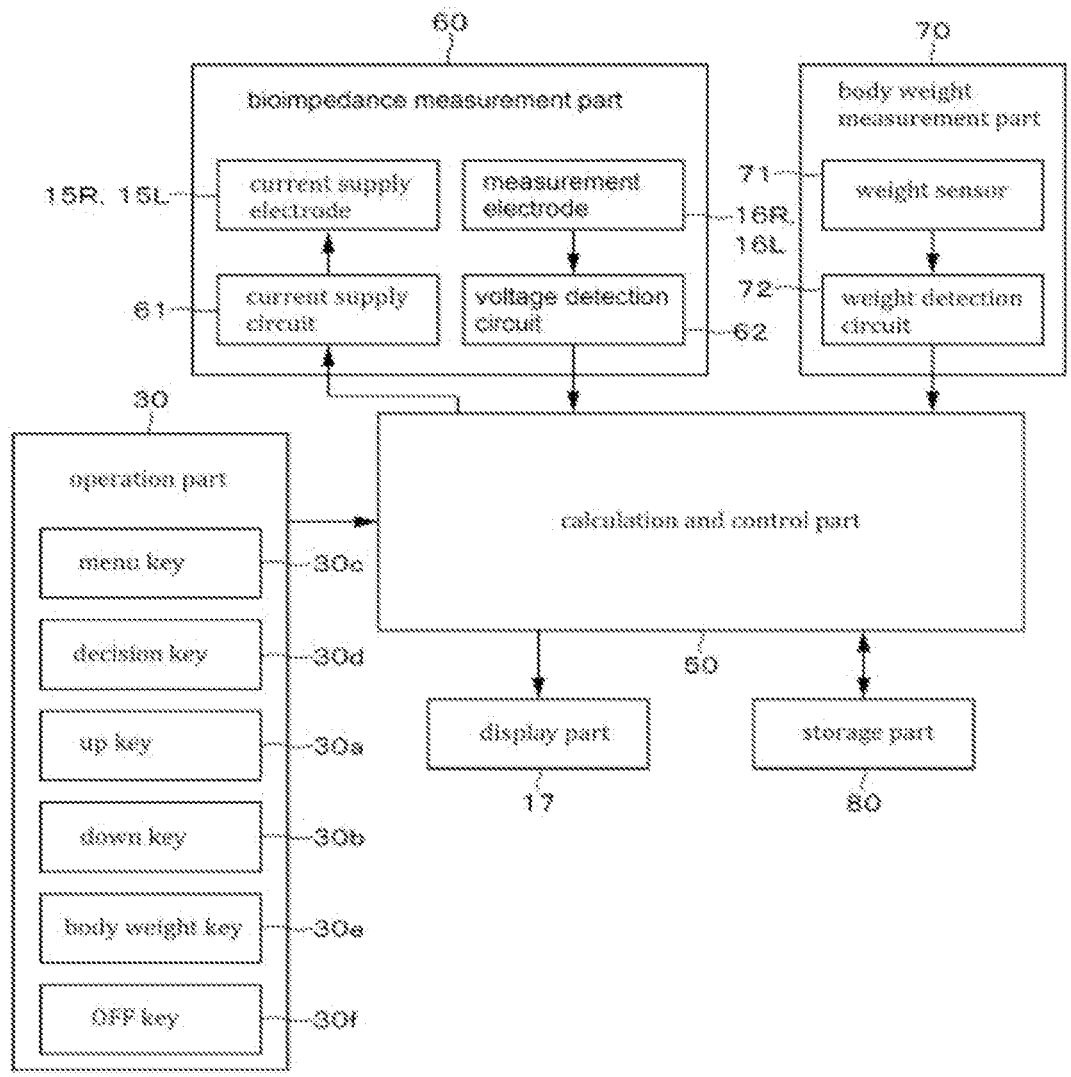
FIG. 3 is a block diagram illustrating an example of an internal structure of the body composition analyzer according to the embodiment.

Next, an example of an internal structure of the body composition analyzer 1 according to the embodiment is described. FIG. 3 is a block diagram illustrating an example of the internal structure of the body composition analyzer 1 according to the embodiment. In addition to the display part 17 and the operation part 30 described above, the body composition analyzer 1 includes a calculation and control part 50 (hereinafter, abbreviated as the control part 50 as appropriate), a bioimpedance measurement part 60, a body weight measurement part 70, and a storage part 80. Since the details of the display part 17 and the operation part 30 have already been described, the description thereof is omitted here.

The control part 50 integrally controls the parts of the body composition analyzer 1 based on a program. The control part 50 determines a degree of matching with respect to a purpose of use that is set in measured data related to multiple body compositions, based on a purpose-of-use matching degree relationship in which a degree of matching with respect to a purpose of use is associated according to a combination relationship about change directions of data related to multiple body compositions associated by a display order with respect to the purpose of use. an operation signal according to an operation input with respect to the operation part 30 is supplied to the control part 50. The control part 50 executes control according to the operation signal. In addition to this, the control part 50 executes commonly known control. Details of a process performed by the control part 50 will be described later.

The bioimpedance measurement part 60 includes a current supply circuit 61 and voltage detection circuit 62, and the above-described current supply electrodes (15R, 15L) and voltage measurement electrodes (16R, 16L). When a user gets on the stand 10, the current supply circuit 61 applies a weak high-frequency constant current to the soles of the user's feet via the current supply electrode (15R) and the current supply electrode (15L) formed on the upper surface 11 of the stand. The voltage detection circuit 62 detects a potential difference via the voltage measurement electrode (16R) and the voltage measurement electrode (16L) and outputs the potential difference to the control part 50.

The body weight measuring part 70 includes, for example, a weight sensor 71 and a weight detection circuit 72. For the weight sensor 71, for example, a load cell formed of a strain-generating body and a strain gauge can be applied. It is structured that one end of the strain-generating body is supported inside the stand 10 and the other end of the strain-generating body is supported by a leg part (not illustrated in the drawings) on a back side of the stand 10. When the strain-generating body bends due to a load when the user gets on the upper surface 11 of the stand 10, the strain gauge expands or contracts, and a resistance value (output value) changes according to the expansion or contraction of the strain gauge. The body weight can be measured by using the change in resistance value as a change in load signal output. A signal output from the weight sensor 71 is converted into weight data by the weight detection circuit 72 and is output to the control part 50.

The storage part 80 includes, for example, a ROM (Read Only Memory), a RAM (Random Access Memory), and a rewritable memory. The ROM is a non-volatile memory, and programs for causing the control part 50 to execute various processes are stored in the ROM. Further the ROM stores formulas for calculating body fat percentage, body age, basal metabolic rate, visceral fat level, muscle mass, estimated bone mass, BMI and body weight. As these programs, programs stored in a storage device different from the ROM, for example, an optical storage medium such as a hard disk or a compact disk, can also be used.

The RAM functions as a work area of the control part 50. In the rewritable memory, personal data such as height, age and gender, and previously measured body composition data is stored in association with identification information that identifies an individual.

Further, in the storage part 80, display order data and advice information, which are associated with a purpose of use, are stored. The display order data is data in which a display order of measured body composition data is defined.

Figure 4:
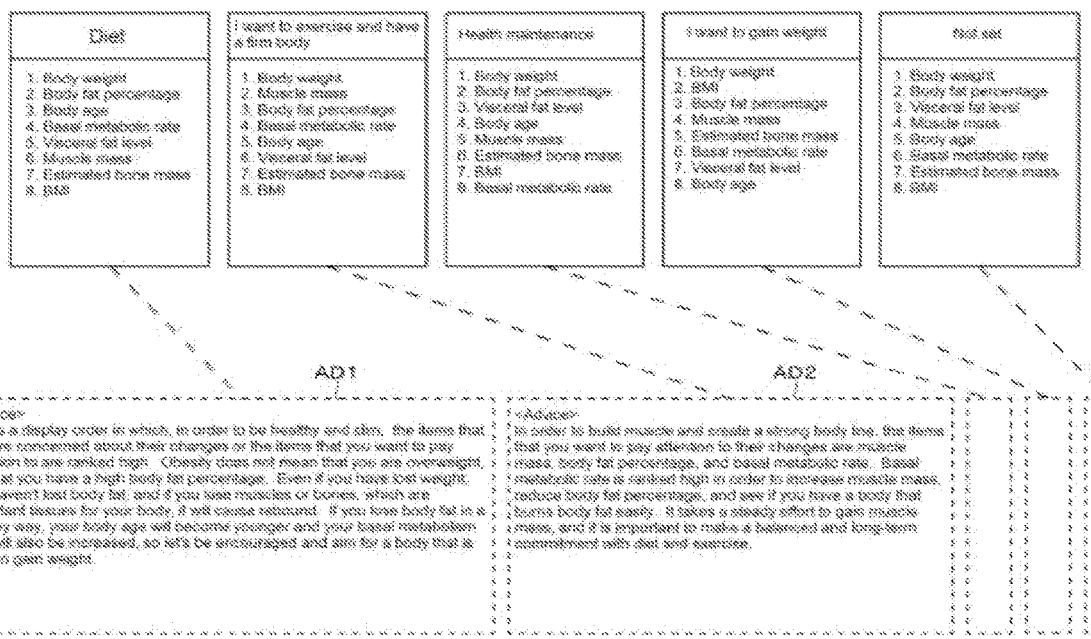
FIG. 4 illustrates an example of display order data and advice information, which are associated with a purpose of use.

FIG. 4 illustrates display order data and advice information, which are associated with a purpose of use. As illustrated in FIG. 4, display order data, in which measurement results are displayed in the order of body weight, body fat percentage, body age, basal metabolic rate, visceral fat level, muscle mass, estimated bone mass, and BMI, is associated with "Diet," which is one of purposes of use of the body composition analyzer 1. Display order data, in which measurement results are displayed in the order of body weight, muscle mass, body fat percentage, basal metabolic rate, body age, visceral fat level, estimated bone mass, and BMI, is associated with "I want to exercise and have a firm body," which is one of the purposes of use of the body composition analyzer 1. Display order data, in which measurement results are displayed in the order of body weight, body fat percentage, visceral fat level, body age, muscle mass, estimated bone mass, BMI, and basal metabolic rate, is associated with "Health maintenance," which is one of the purposes of use of the body composition analyzer 1. Display order data, in which measurement results are displayed in the order of body weight, BMI, body fat percentage, muscle mass, estimated bone mass, basal metabolic rate, visceral fat level, and body age, is associated with "I want to gain weight," which is one of the purposes of use of the body composition analyzer 1. When a purpose of use of the body composition analyzer 1 is "Not set," display order data, in which measurement results are displayed in the order of body weight, body fat percentage, visceral fat level, muscle mass, body age, basal metabolic rate, estimated bone mass, and BMI, is associated. The display order data is specified to be an order of the body compositions that is considered important with respect to each purpose of use.

Further, for each purpose of use, in addition to the display order data, advice information with a content corresponding to the purpose of use is associated. As illustrated in FIG. 4, for example, advice information (AD1) is associated with "Diet," which is one of the purposes of use. Further, for "I want to exercise and have a firm body," which is one of the purposes of use, advice information (AD2) is associated.

Although not illustrated in the drawing, predetermined advice information is associated with each of the purposes of use "Health maintenance," "I want to gain weight" and "Not set."

Further, the storage part 80 stores a purpose-of-use matching degree relationship. The purpose-of-use matching degree relationship is a relationship in which a degree of matching with respect to a purpose of use is associated according to a combination relationship about change directions of data related to multiple body compositions associated by a display order with respect to the purpose of use. In other words, it is a relationship in which, in an order from data related to a body composition that is most important with respect to the purpose of use, each change direction division of data related to a body composition is associated with change direction divisions of data related to a body composition next in the order.

FIG. 5 illustrates an example of the purpose-of-use matching degree relationship corresponding to the purpose of use "Diet." The purpose-of-use matching degree relationship illustrated in FIG. 5 is a purpose-of-use matching degree relationship that is used when a male user is on a diet, that is, a purpose-of-use matching degree relationship for male users.

When a purpose of use is "Diet," a degree of matching with respect to "Diet" is associated according a combination relationship about change directions of "body fat percentage (%)," "body age" and "basal metabolic rate" that are associated by a display order with respect to "Diet." Here, "body fat percentage (%)," "body age" and "basal metabolic rate" are body composition analyzer data in a descending order of importance with respect to the purpose of use "Diet." That is, the purpose-of-use matching degree relationship corresponding to the purpose of use "Diet" in the present example is a relationship in which, in an order from data related to a body composition that is most important with respect to the purpose of use "Diet" (in the present example, "body fat percentage (%)"), each change direction division of "body fat percentage (%)" is associated with change direction divisions of data related to a body composition next in the order (in the present example, "body age"), and each change direction division of "body age" is associated with change direction divisions of data related to a body composition next in the order (in the present example, "basal metabolic rate").

As illustrated in FIG. 5, a degree of matching with respect to "Diet" is associated according to a combination relationship of change directions. A degree of matching in the present example is a purpose matching degree evaluation rank order associated with a combination relationship of change directions and purpose matching degree evaluation data obtained by scoring the purpose matching degree evaluation rank order. The purpose matching degree evaluation data is displayed as a body composition change comprehensive evaluation.

The purpose-of-use matching degree relationship is further associated with advice information according to the degree of matching with respect to the purpose of use. FIG. 6A illustrates an example of advice information when the purpose of use is "Diet," "body fat percentage (%)," "body age" and "basal metabolic rate" show favorable changes with respect to "Diet," and the purpose matching degree evaluation rank order is high (for example, the purpose matching degree evaluation rank order is 1st or 2nd place). Further, FIG. 6B illustrates an example of advice information when the purpose of use is "Diet," and the purpose matching degree evaluation rank order is a medium rank order, specifically, a rank order that "body fat percentage (%)" has decreased but "basal metabolic rate" has also decreased (the purpose matching degree evaluation rank order is 3rd, 6th or 9th place).

[Operation Example of Body Composition Analyzer]
(Setting Mode)

Figure 7:
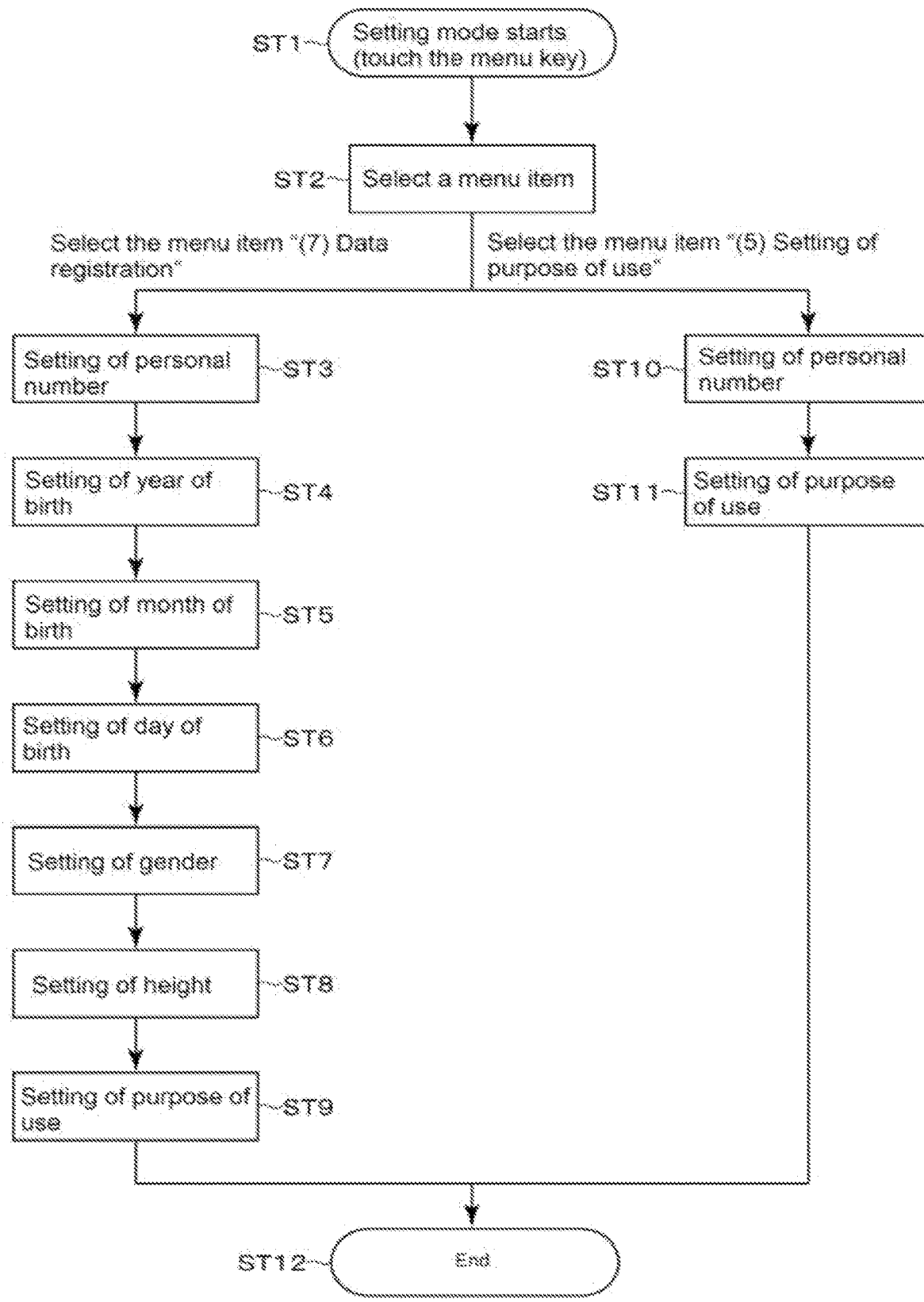
FIG. 7 is a flowchart that is referenced when an operation example of the body composition analyzer in a setting mode is described.

Next, an operation example of the body composition analyzer 1 is described. First, with reference to a flowchart illustrated in FIG. 7, an operation example of the body composition analyzer 1 in a setting mode in which various settings with respect to the body composition analyzer 1 are performed is described. A process described below is executed under the control of the control part 50 according to inputs to the operation part 30. Setting contents are stored in the storage part 80. In the following description, user information that can be set by the setting mode (information about personal number, date of birth, and gender, and the like, which will be described later) may be referred to as attributes.

In Step ST1, by touching the touch switch (30c) (menu key), menu items are displayed on the display part 17. Then, the process proceeds to Step ST2.

In Step ST2, the menu items can be switched by a user operation. The menu items can be switched by touching the touch switch (30a) (up key) or the touch switch (30b) (down key), and a menu item is set by touching the touch switch (30d) (decision key).

In Step ST2, when a menu item (7) (data registration) is set, the process proceeds to Step ST3. In Step ST3, a personal number setting screen is displayed on the display part 17, and a personal number is set. The personal number is an identification number among users (such as family members) using the same body composition analyzer 1, and is, for example, an integer from 1 to 5. In this case, up to 5 users can be registered. After an identification number is selected by touching the touch switch (30a) (up key) or the touch switch (30b) (down key), a personal number is set by touching the touch switch (30d) (decision key). Then, the process proceeds to Step ST4.

In Step ST4, the year of birth of the user is set. The year of birth can be set, for example, using the western calendar. After the year is selected by touching the touch switch (30a) (up key) or the touch switch (30b) (down key), the year of birth of the user is set by touching the touch switch (30d) (decision key). Then, the process proceeds to Step ST5.

In Step ST5, the month of birth of the user is set. After the month is selected by touching the touch switch (30a) (up key) or the touch switch (30b) (down key), the month of birth of the user is set by touching the touch switch (30d) (decision key). Then, the process proceeds to Step ST6.

In Step ST6, the day of birth of the user is set. After the day is selected by touching the touch switch (30a) (up key) or the touch switch (30b) (down key), the day of birth of the user is set by touching the touch switch (30d) (decision key). Then, the process proceeds to Step ST7.

In Step ST7, the gender of the user is set. After the gender is selected by touching the touch switch (30a) (up key) or the touch switch (30b) (down key), the gender of the user is set by touching the touch switch (30d) (decision key). Then, the process proceeds to Step ST8.

In Step ST8, the height of the user is set. After the height (numerical value) is selected by touching the touch switch (30a) (up key) or the touch switch (30b) (down key), the height of the user is set by touching the touch switch (30d) (decision key). Then, the process proceeds to Step ST9.

In Step ST9, a purpose of use of the body composition analyzer 1 is set. The term "purpose of use" refers to how a user who uses the body composition analyzer 1 wants to manage his/her body, and in the present embodiment, four purposes of use, "Diet," "I want to exercise and have a firm body," "Health maintenance" and "I want to gain weight," can be set. Further, it is also possible to "not set" a purpose of use. After a purpose of use is selected by touching the touch switch (30*a*) (up key) or the touch switch (30*b*) (down key), the purpose of use of the body composition analyzer 1 is set by touching the touch switch (30*d*) (decision key). Then, the process proceeds to Step ST12, and the process of setting various information is completed.

The process of Steps ST3-ST9 described above is performed, for example, as an initial registration at the first use after the body composition analyzer 1 is purchased.

In Step ST2, when a menu item (5) (setting of a purpose of use) is selected, the process proceeds to Step ST10. In Step ST10, setting of a personal number is performed. In the setting of a personal number in Step ST10, a personal number of which attributes have already been registered is selected. When a personal number is selected, the process proceeds to Step ST11.

In Step ST11, by performing the same operation as in Step ST9, a purpose of use of the body composition analyzer 1 is set. Then, the process proceeds to Step ST12, and the process of setting a new purpose of use or changing a purpose of use is completed.

By performing the process of Steps ST10 and ST11, even when a purpose of use of the body composition analyzer 1 is not set at the time of initial registration, the purpose of use can be set later. Further, even when a purpose of use of the body composition analyzer 1 is set at the time of initial registration, the user can change the purpose of use of the body composition analyzer 1 according to a change in life rhythm or the like.

(Measurement Mode)

Figure 8:
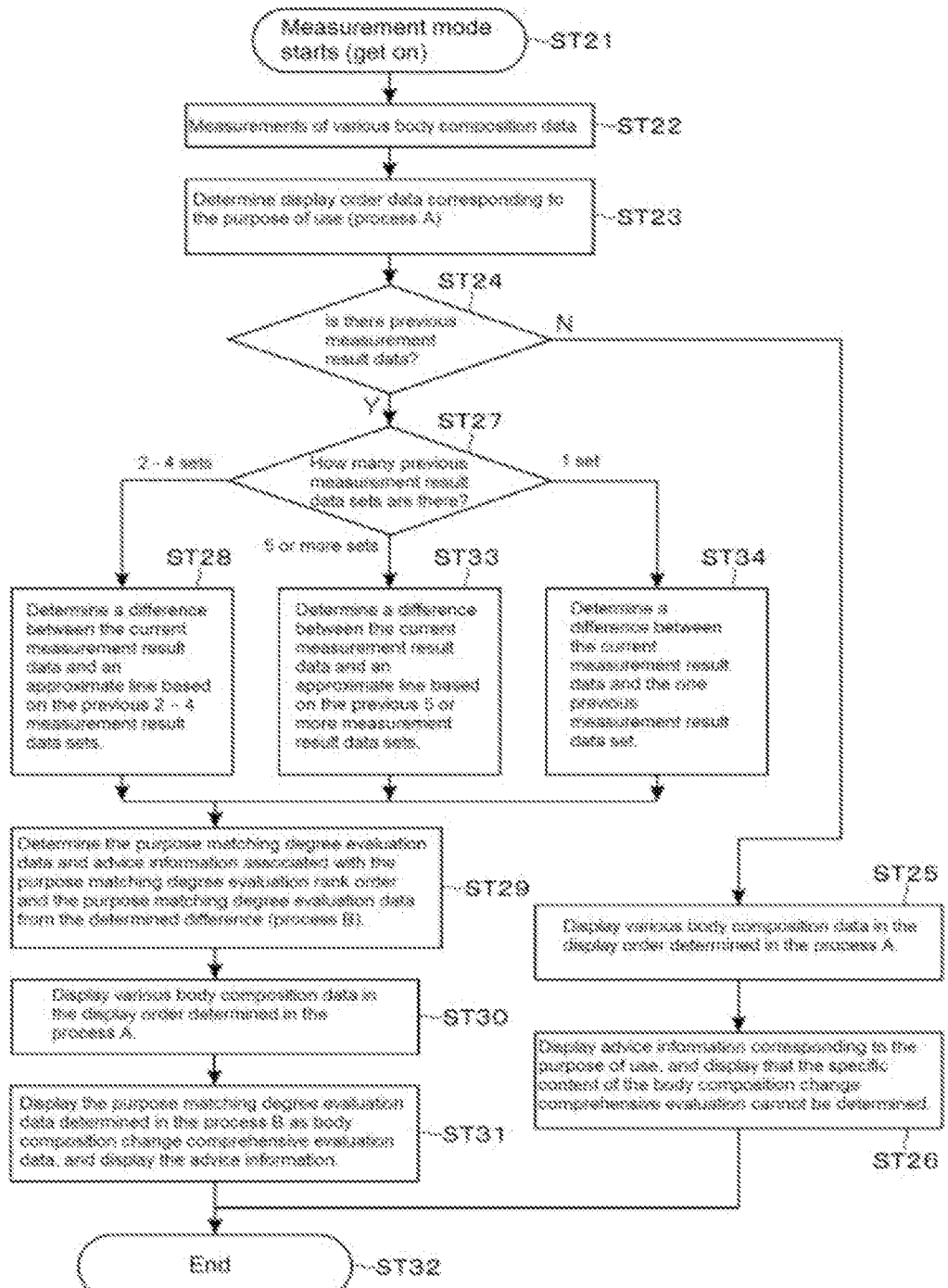
FIG. 8 is a flowchart that is referenced when an operation example of the body composition analyzer in a measurement mode is described.

Next, with reference to a flowchart illustrated in FIG. 8, an operation example of the body composition analyzer 1 in a measurement mode is described.

In Step ST21, in response to an action of a user of getting on the upper surface 11 of the stand 10, a process of the measurement mode starts in the body composition analyzer 1. In the present example, a description is given assuming that a user with registered attributes has gotten on the body composition analyzer 1. The personal number, which is one of the attributes, may be input when the user gets on the body composition analyzer 1, or may be automatically recognized by the body composition analyzer 1. Then, the process proceeds to Step ST22.

In Step ST22, the body weight and the bioimpedance are measured by the body composition analyzer 1, and, by calculations using these informations, measurements of various body composition data are performed. The body composition data measured at this stage is referred to as the user's current measurement result data as appropriate. Further, the user's body composition data that is previously measured and is stored in the storage part 80 is referred to as previous measurement result data as appropriate. Then, the process proceeds to Step ST23.

In Step ST23, the control part 50 determines a purpose of use corresponding to the personal number and determines display order data corresponding to the determined purpose of use. In the following description, the process of determining the display order data is referred to as a process (A) as appropriate. Then, the process proceeds to Step ST24.

In Step ST24, the control part 50 refers to information stored in the storage part 80, and determines whether or not there is previous measurement result data corresponding to the personal number. When there is no previous measurement result data corresponding to the personal number, the process proceeds to Step ST25.

In Step ST25, the measurement result data of the body compositions measured in Step ST22 is displayed on the display part 17 in a display order based on the display order data determined in the process (A) described above. Then, the process proceeds to Step ST26.

In Step ST26, after the measurement results of the body compositions are displayed, advice information associated with the purpose of use is displayed. Then, the process proceeds to Step ST32, and the series of processes is completed.

In the determination process of Step ST24, when previous measurement result data is stored in the storage part 80, the process proceeds to Step ST27. In Step ST27, the control part 50 determines an existence state of previously measured measurement result data related to the multiple body compositions, specifically, the number of previous measurement result data sets stored in the storage part 80. When there are 2-4 previous measurement result data sets, the process proceeds to Step ST28.

In Step ST28, the control part 50 determines an approximate line using measurement result data previously measured within a predetermined time period as samples. An example is considered in which, for example, three previous measurement result data sets for each body composition are stored in the storage part 80. The control part 50 determines for each body composition an approximate line using the three previous measurement result data sets. The approximate line is a straight line obtained by plotting the three previous measurement result data sets with the horizontal axis as a time axis and the vertical axis as the measurement result data of the body composition, and applying a least square method or the like to it. Then, the control part 50 determines a difference between the current measurement result data and measurement result data on the approximate line corresponding to the present "the current measurement result data"—"measurement result data on the approximate line corresponding to the present"). Then, the process proceeds to Step ST29.

In Step ST29, the control part 50 determines a changing trend of each body composition from the difference determined in Step ST28. For example, the control part 50 determines that it is a "no change" when the difference is within a certain range, it is a "+change" when the difference is "+" and is equal to or greater than a certain value, and it is a "−change" when the difference is "−" and is equal to or greater than a certain value. Based on the purpose-of-use matching degree relationship, the control part 50 determines a purpose matching degree evaluation rank order according to a combination relationship of a changing trend of each body composition, and determines purpose matching degree evaluation data obtained by scoring the purpose matching degree evaluation rank order. For example, when the changing trend of "body fat percentage (%)" is "−change," the changing trend of "body age" is "−change," and the changing trend of "basal metabolic rate" is "+change," the purpose matching degree evaluation rank order is "1st place," and the purpose matching degree evaluation data is "100 points" (see FIG. 5).

Further, in the process of Step ST29, evaluation (for example, scoring) with respect to the changing trend is performed for each body composition. For example, regarding "body fat percentage," when the changing trend based on the difference determined in Step ST28 is "−change," a high score is assigned, when the changing trend based on the difference determined in Step ST28 is "no change," a medium score is assigned, and when the changing trend based on the difference determined in Step ST28 is "+change," a low score is assigned.

Further, the control part 50 determines advice information associated with the purpose matching degree evaluation rank order and the purpose matching degree evaluation data. In the following description, the process of Step ST29 is referred to as a "process (B)" as appropriate. When the process of Step ST29 is completed, the process proceeds to Step ST30.

In Step ST30, the current measurement result data of each body composition is displayed based on the display order data determined in the process (A) described above. Then, the process proceeds to Step ST31.

In Step ST31, the control part 50 displays the purpose matching degree evaluation data and the advice information, which are determined in the process (B). Then, the process proceeds to Step ST32, and the series of processes is completed.

In the determination process of Step ST27, when the number of previous measurement result data sets is 5 or more, the process proceeds to Step ST33.

In Step ST33, the control part 50 determines an approximate line using measurement result data previously measured within a predetermined time period as samples. An example is considered in which, for example, ten previous measurement result data sets for each body composition are stored in the storage part 80. The control part 50 determines for each body composition an approximate line using the ten previous measurement result data sets. The approximate line is a straight line obtained by plotting the ten previous measurement result data sets with the horizontal axis as a time axis and the vertical axis as the measurement result data of the body composition, and applying a least square method or the like to it. Then, the control part 50 determines a difference between the current measurement result data and measurement result data on the approximate line corresponding to the present "the current measurement result data"—"measurement result data on the approximate line corresponding to the present"). Then, the process proceeds to Step ST29.

Since the specific contents of the processes of Steps ST29-ST31 have already been described, only a brief description is given. In Step ST29, the control part 50 determines a changing trend of each body composition from the difference determined in Step ST33. Further, based on the purpose-of-use matching degree relationship, the control part 50 determines a purpose matching degree evaluation rank order according to a combination relationship of a changing trend of each body composition, and determines purpose matching degree evaluation data obtained by scoring the purpose matching degree evaluation rank order. Further, in the process of Step ST29, evaluation (for example, scoring) with respect to the changing trend is performed for each body composition. Further, the control part 50 determines advice information associated with the purpose matching degree evaluation rank order and the purpose matching degree evaluation data. Then, the process proceeds to Step ST30.

In Step ST30, the current measurement result data of each body composition is displayed based on the display order data determined in the process (A) described above. The process proceeds to Step ST31.

In Step ST31, the control part 50 displays the purpose matching degree evaluation data and the advice information, which are determined in the process (B). Then, the process proceeds to Step ST32, and the series of processes is completed.

In the determination process of Step ST27, when there is no more than one previous measurement result data set, in other words, when there is only one previous measurement result data set, the process proceeds to Step ST34. In Step ST34, a difference between the current measurement result data and the one previous measurement result data set is determined. Then, the process proceeds to Step ST29.

In Step ST29, based on the difference determined in Step ST34, the control part 50 determines a changing trend of each body composition. For example, the control part 50 determines that it is a "no change" when the difference determined in Step ST34 is within a certain range, it is a "+change" when the difference is "+" and is equal to or greater than a certain value, and it is a "−change" when the difference is "−" and is equal to or greater than a certain value. Then, based on the purpose-of-use matching degree relationship, the control part 50 determines a purpose matching degree evaluation rank order according to a combination relationship of a changing trend of each body composition, and determines purpose matching degree evaluation data obtained by scoring the purpose matching degree evaluation rank order. Further, in the process of Step ST29, evaluation (for example, scoring) with respect to the changing trend is performed for each body composition. Further, the control part 50 determines advice information associated with the purpose matching degree evaluation rank order and the purpose matching degree evaluation data. Then, the process proceeds to Step ST30.

In Step ST30, the current measurement result data of each body composition is displayed based on the display order data determined in the process (A) described above. Then, the process proceeds to Step ST31.

In Step ST31, the control part 50 displays the purpose matching degree evaluation data and the advice information, which are determined in the process (B). Then, the process proceeds to Step ST32, and the series of processes is completed.

FIG. 9 illustrates a specific display example of the process of Step ST25 described above when "Diet" is set as the purpose of use. Since "Diet" is set as the purpose of use, the measurement result data of the body compositions is displayed in the order (body weight→body fat percentage→body age→basal metabolic rate→visceral fat→muscle mass→estimated bone mass→BMI) illustrated by <1>-<8> in FIG. 9 according to the display order data associated with "Diet."

FIG. 10 illustrates a specific display example of the process of Step ST26 when "Diet" is set as the purpose of use. As illustrated in FIG. 10, the advice information (AD1) associated with the purpose of use "Diet" is displayed on the display part 17. In Step ST26, there is no previous measurement result data and purpose matching degree evaluation data cannot be determined. Therefore, in Step ST26, as illustrated in FIG. 10, it is displayed that a specific content of "body composition change comprehensive evaluation" cannot be determined this time, in other words, a comment (C1) indicating that "body composition change comprehensive evaluation" will be determined from next time is displayed.

FIG. 11 illustrates a specific display example of the process of Step ST30 described above when "Diet" is set as the purpose of use. Since "Diet" is set as the purpose of use, the current measurement result data is displayed in the order (body weight→body fat percentage→body age→basal metabolic rate→visceral fat→muscle mass→estimated bone mass→BMI) illustrated by <1>-<8> in FIG. 11 according to the display order data associated with "Diet." Further, in Step ST30, it is displayed in association with the changing trend for each body composition determined in Step ST29. That is, when the changing trend of the body composition is "no change," "→" is displayed next to the display indicating the type of the body composition, when the changing trend of the body composition is "+change," "↑" is displayed next to the display indicating the type of the body composition, and when the changing trend of the body composition is "−change," "↓" is displayed next to the display indicating the type of the body composition.

FIG. 12 illustrates a specific display example of the process of Step ST31 described above when "Diet" is set as the purpose of use. As illustrated in FIG. 12, the control part 50 displays advice information (AD5) in an upper half of the display part 17. Further, the control part 50 displays an item "body composition change comprehensive evaluation" below the advice information (AD5), and displays a score of "90 points," which is the purpose matching degree evaluation data, on a right side of the item. Further, the control part 50 displays, in descending order of importance, "body fat percentage," "body age" and "basal metabolism," which are body compositions that are highly important for the purpose of use "Diet," below the item "body composition change comprehensive evaluation." Then, next to the display indicating the type of the body composition, the arrow corresponding to the changing trend determined in Step ST29, a bar having a length corresponding to a score of the body composition assigned with respect to the changing trend, and the specific score are displayed. In the example illustrated in FIG. 12, for example, the arrow "↓" indicating a changing trend of "−change" is displayed on a right side of "body fat percentage," a bar "*****" is displayed on a right side of the arrow "↓," and on a further right side thereof, a score of "99 points," which is the score assigned to the changing trend of "body fat percentage," is displayed. The bar is displayed such that the higher the score, the longer it extends to the right.

According to the present embodiment described above, whether a change occurring in one's body is in a good direction or not can be determined according to a purpose of use of the body composition analyzer. Since a determination result is displayed to a user, even when the user has no professional knowledge, the user can get a clue as to whether or not a physical change based on a daily life trend or a direction of effort is suitable for a purpose of use, and can grasp a substantial meaning of a measurement result. Therefore, since not only is it easier for a user to get a sense of change, but it is also easier for the user to make an effort toward his/her goal or improve his/her live for a long time, the body composition analyzer is effective in maintaining motivation, and can also be effectively used for guidance in sports gyms or facilities for beauty purposes.

Modified Embodiments

The embodiment of the present invention has been described. However, the present invention is not limited to the above-described embodiment, and various modifications can be made within the scope of the technical idea of the present invention. In the following, modified embodiments are described.

FIG. 13 illustrates another example of a purpose-of-use matching degree relationship. The example illustrated in FIG. 13 is an example of a purpose-of-use matching degree relationship when the purpose of use of the body composition analyzer 1 is "I want to exercise and have a firm body." "Muscle mass," "body fat percentage" and "basal metabolic rate" in a descending order of importance are used as the multiple body compositions for the purpose-of-use matching degree relationship when the purpose of use is "I want to exercise and have a firm body."

FIG. 14 illustrates an example of advice information associated with the purpose-of-use matching degree relationship when the purpose of use is "I want to exercise and have a firm body." Specifically, it is an example of advice information in which there is no significant change in user's body compositions and the purpose matching degree evaluation data is associated with a medium score (for example, a score corresponding to the 14th place in the purpose matching degree evaluation rank order of the purpose-of-use matching degree relationship illustrated in FIG. 13).

FIG. 15 illustrates another example of a purpose-of-use matching degree relationship. The example illustrated in FIG. 15 is an example of a purpose-of-use matching degree relationship when the purpose of use of the body composition analyzer 1 is "Health maintenance." "Body fat percentage," "visceral fat level" and "body age" in a descending order of importance are used as the multiple body compositions for the purpose-of-use matching degree relationship when the purpose of use is "Health maintenance."

The example illustrated in FIG. 16 is an example of a purpose-of-use matching degree relationship when the purpose of use of the body composition analyzer 1 is "Diet." Even when the purpose of use is the same, there is a difference that the purpose-of-use matching degree relationship illustrated in FIG. 5 is for men, whereas the purpose-of-use matching degree relationship illustrated in FIG. 16 is for women. When the user is a woman, during a period when the user's body is swelling, even when the body fat mass decreases, the body weight increases, and thus, the body fat percentage in the total body weight does not decrease. In consideration of such a case, in the case of women, appropriate evaluation can be performed by using "body fat mass" instead of "body fat percentage." Therefore, when a personal attribute set in the setting mode is "female," even when the purpose of use is the same, the purpose-of-use matching degree relationship illustrated in FIG. 16 is used. In this way, even when the purpose of use is the same, the purpose-of-use matching degree relationship to be used may be changed according to a personal attribute.

In the above-described embodiment, an approximate line based on measurement result data previously measured within a predetermined time period is determined, and a difference between the current measurement result data and measurement result data on the approximation line corresponding to the present is determined. The user may be able to set the predetermined time period. In general, to evaluate whether or not a physical change is a change that matches "Diet," previous measurement result data over a long time period to some extent is required. However, during the time period, it is also possible that the user behaves contrary to the purpose of use. For example, even when the purpose of use is "Diet," there may be a time period during which the user overeats. It is preferable to exclude such a time period, that is, to use measurement result data of a time period during which the user is seriously engaged in dieting. Therefore, the user may be able to set a range of use of the previous measurement result data (for example, within the last week or by specifying a date range).

In the above-described embodiment, when variation in the previous measurement result data is large, a comment such as "Regularity of the measurement results is not good" or "It looks like you are having an eventful life. Please review your life rhythm" may be displayed.

In the above-described embodiment, the purpose matching degree evaluation data or the advice information is displayed after the measurement result data of the body compositions is displayed. However, the purpose matching degree evaluation data or the advice information may be displayed first. Since it requires a certain time period to display all the measurement result data of the body compositions, the purpose matching degree evaluation data or the advice information may be displayed to the user first. Further, it is also possible that the purpose matching degree evaluation data or the advice information is displayed first, and the measurement result data of the body compositions is displayed only when a predetermined operation is performed. Further, it is also possible that the user is allowed to set whether to display the purpose matching degree evaluation data or the advice information or the measurement result data of the body compositions first. As a result, the user can display information that he/she is interested in first.

Even when there is no previous measurement result data stored in the storage part 80, the current measurement result data may be compared with an average value of measurement result data of a body composition about a certain attribute. Then, a changing trend may be determined from a difference between the current measurement result data and the average value, the changing trend may be scored, and the score may be displayed.

The information displayed in Step S31 may be changed according to the number of the previous measurement result data sets. For example, when the number of the previous measurement result data sets is 5 or more, it may be displayed in Step ST31 that the reliability of the body composition change comprehensive evaluation is high. Conversely, when there is only one previous measurement result data set, it may be displayed in Step ST31 that the reliability of the body composition change comprehensive evaluation is low.

The degree of matching associated with the purpose-of-use matching degree relationship may be other than the purpose matching degree evaluation rank order or the purpose matching degree evaluation data, and may be any indicator indicating the degree of matching. Further, in the above-described embodiment, in determining whether or not it matches with respect to the purpose of use, the number of body compositions in a descending order of importance is set to 3. However, the number of body compositions may be 2, or 4 or more.

Structures that can be gripped with the left and right hands may be added to the body composition analyzer 1 of the embodiment described above, an electrode for the left hand and an electrode for the right hand may be arranged on portions gripped by the hands, and impedance may be measured through the hands and the feet.

A structure different from the structure illustrated in FIG. 3 may be added to the body composition analyzer 1. For example, a communication module that performs near-field wireless communication with a mobile device such as a smartphone or a communication module for connecting to a network such as the Internet may be added to the body composition analyzer 1. All or part of the calculations performed by the body composition analyzer 1 may be performed on a smartphone or on a server device on a cloud.

Further, the purpose matching degree evaluation data or the advice information may be reproduced by voice.

DESCRIPTION OF REFERENCE NUMERALS

1: body composition analyzer, 17: display part, 30: operation part, 50: calculation and control part

The invention claimed is:
1. A biometric information measuring device, comprising:
    a body composition data acquisition part comprising circuitry configured to acquire data related to a body composition of a user; and
    a control part comprising circuitry configured to obtain a purpose of use by the user and evaluate whether changes in data of the body composition match the purpose of use.
2. The biometric information measuring device according to claim 1, wherein the circuitry of the control part is configured to generate an advice according to a change in the data related to the body composition.
3. The biometric information measuring device according to claim 2, wherein the circuitry of the control part is configured to determine a degree of matching with respect to the purpose of use set in measured data related to multiple body compositions, based on a purpose-of-use matching degree relationship in which the degree of matching with respect to the purpose of use is associated according to a combination relationship about change directions of data related to the multiple body compositions associated by a display order with respect to the purpose of use.
4. The biometric information measuring device according to claim 3, wherein the circuitry of the control part is configured to determine the degree of matching with respect to the purpose of use set in currently measured data related to the multiple body compositions according to an existence state of previously measured data related to the multiple body compositions.
5. The biometric information measuring device according to claim 3, wherein in the purpose-of-use matching degree relationship, advice information is further associated according to the degree of matching with respect to the purpose of use, and based on the purpose-of-use matching degree relationship in which the advice information is further associated, the circuitry of the control part is configured to determine advice information with respect to the degree of matching.
6. The biometric information measuring device according to claim 3, wherein for each measured data related to the multiple body compositions, the circuitry of the control part is configured to determine the degree of matching with respect to change directions of the data and the purpose of use.
7. The biometric information measuring device according to claim 1, wherein the circuitry of the control part is configured to determine a degree of matching with respect to the purpose of use set in measured data related to multiple body compositions, based on a purpose-of-use matching degree relationship in which the degree of matching with respect to the purpose of use is associated according to a combination relationship about change directions of data related to the multiple body compositions associated by a display order with respect to the purpose of use.
8. The biometric information measuring device according to claim 7, wherein the circuitry of the control part is configured to determine the degree of matching with respect to the purpose of use that is set in currently measured data related to the multiple body compositions according to an existence state of previously measured data related to the multiple body compositions.

9. The biometric information measuring device according to claim 7, wherein in the purpose-of-use matching degree relationship, advice information is further associated according to the degree of matching with respect to the purpose of use, and based on the purpose-of-use matching degree relationship in which the advice information is further associated, the circuitry of the control part is configured to determine advice information with respect to the degree of matching.

10. The biometric information measuring device according to claim 7, wherein for each measured data related to the multiple body compositions, the circuitry of the control part is configured to determine the degree of matching with respect to change directions of the data and the purpose of use.

11. The biometric information measuring device according to claim 1, further comprising:
a storage part comprising circuitry configured to store information on a plurality of body composition items selected for each of possible intended uses of the biometric information measuring device, and information on an intended use match relationship in which a degree of match for each of the possible intended uses is associated with each of patterns generated by combining the information on the plurality of body composition items and information on a tendency of change for each of the body composition items, wherein the circuitry of the control part is configured to determine a degree that a use of the biometric information measuring device by the user matches a specific intended use by the user based on a pattern generated by combining the tendency of change for each of the body composition items for the user and corresponding to one of the patterns stored in the storage part.

12. A biometric information measuring system, comprising:
a body composition data acquisition part comprising circuitry configured to acquire data related to a body composition of a user; and
a control part comprising circuitry configured to obtain a purpose of use by the user and evaluate whether changes in data of the body composition matches the purpose of use.

13. The biometric information measuring system according to claim 12, wherein the circuitry of the control part is configured to generate an advice according to a change in the data related to the body composition.

14. The biometric information measuring system according to claim 13, wherein the circuitry of the control part is configured to determine a degree of matching with respect to the purpose of use set in measured data related to multiple body compositions, based on a purpose-of-use matching degree relationship in which the degree of matching with respect to the purpose of use is associated according to a combination relationship about change directions of data related to the multiple body compositions associated by a display order with respect to the purpose of use.

15. The biometric information measuring system according to claim 12, wherein the circuitry of the control part is configured to determine a degree of matching with respect to the purpose of use set in measured data related to multiple body compositions, based on a purpose-of-use matching degree relationship in which the degree of matching with respect to the purpose of use is associated according to a combination relationship about change directions of data related to the multiple body compositions associated by a display order with respect to the purpose of use.

16. The biometric information measuring system according to claim 15, wherein the circuitry of the control part is configured to determine the degree of matching with respect to the purpose of use set in currently measured data related to the multiple body compositions according to an existence state of previously measured data related to the multiple body compositions.

17. The biometric information measuring system according to claim 15, wherein in the purpose-of-use matching degree relationship, advice information is further associated according to the degree of matching with respect to the purpose of use, and based on the purpose-of-use matching degree relationship in which the advice information is further associated, the circuitry of the control part is configured to determine advice information with respect to the degree of matching.

18. The biometric information measuring system according to claim 15, wherein for each measured data related to the multiple body compositions, the circuitry of the control part is configured to determine the degree of matching with respect to change directions of the data and the purpose of use.

19. A method of measuring biometric information,
acquiring data related to a body composition of a user by using a body composition data acquisition part comprising circuitry configured to acquire the data related to the body composition of the user;
obtain a purpose of use by the user by using a control part comprising circuitry configured to obtain the purpose of use by the user; and
evaluating whether changes in data of the body composition matches the purpose of use by using the circuitry of the control part configured to evaluate whether the changes in the data matches the purpose of use.

20. A non-transitory computer-readable recording medium stored thereon a program that when executed by an information processing apparatus, the information processing apparatus executes a biometric information measuring method, the biometric information measuring method comprising:
acquiring data related to a body composition of a user by using a body composition data acquisition part comprising circuitry configured to acquire the data related to the body composition of the user;
obtain a purpose of use by the user by using a control part comprising circuitry configured to obtain the purpose of use by the user; and
evaluating whether changes in data of the body composition matches the purpose of use by using the circuitry of the control part configured to evaluate whether the changes in the data matches the purpose of use.

* * * * *